US012247225B2

United States Patent
Zhang et al.

(10) Patent No.: US 12,247,225 B2
(45) Date of Patent: Mar. 11, 2025

(54) PLACENTAL TISSUE COMPOSITIONS AND METHODS

(71) Applicant: ELUTIA INC., Silver Spring, MD (US)

(72) Inventors: Ji Zhang, North Potomac, MD (US); Daniel Deegan, Silver Spring, MD (US); Darryl Roberts, Doylestown, PA (US)

(73) Assignee: ELUTIA INC., Silver Spring, MD (US)

( * ) Notice: Subject to any disclaimer, the term of this patent is extended or adjusted under 35 U.S.C. 154(b) by 415 days.

(21) Appl. No.: 17/183,927

(22) Filed: Feb. 24, 2021

(65) Prior Publication Data

US 2021/0269775 A1 Sep. 2, 2021

Related U.S. Application Data

(60) Provisional application No. 62/983,060, filed on Feb. 28, 2020.

(51) Int. Cl.
C12N 5/071 (2010.01)
C12M 3/04 (2006.01)

(52) U.S. Cl.
CPC ............. *C12N 5/0682* (2013.01); *C12M 3/04* (2013.01); *C12N 2533/92* (2013.01)

(58) Field of Classification Search
CPC .......................... C12N 5/0682; C12N 2533/92
See application file for complete search history.

(56) References Cited

U.S. PATENT DOCUMENTS

| | | |
|---|---|---|
| 4,902,508 A | 2/1990 | Badylak et al. |
| 5,281,422 A | 1/1994 | Badylak et al. |
| 5,554,389 A | 9/1996 | Badylak et al. |
| 8,231,908 B2 | 7/2012 | Kinoshita et al. |
| 8,372,439 B2 | 2/2013 | Daniel et al. |
| 8,735,054 B1 | 5/2014 | Sun et al. |
| 10,052,351 B2 | 8/2018 | Koob |
| 2009/0246773 A1 | 10/2009 | Caniggia et al. |
| 2010/0028306 A1 | 2/2010 | Clarke et al. |
| 2014/0271728 A1 | 9/2014 | Koob et al. |
| 2015/0216912 A1 | 8/2015 | Koob |
| 2015/0306150 A1 | 10/2015 | Zhang et al. |
| 2015/0320906 A1 | 11/2015 | Broussard |
| 2019/0365948 A1 | 12/2019 | Deegan et al. |

FOREIGN PATENT DOCUMENTS

| | | |
|---|---|---|
| CN | 105688287 A | 6/2016 |
| WO | 2017112934 A1 | 6/2017 |

OTHER PUBLICATIONS

Fratini et al., Canine placenta recellualrized using yolk sac cells with vascular endothelial growth factor. BioResearch Open Access, vol. 7, No. 1 (Jul. 1, 2018) pp. 101-106 (Year: 2018).*

Burke, A., "How long are dogs pregnant" American Kennel Club (May 3, 2021, [online], [retrieved on May 12, 2023]. Retrieved from the Internet: <URL: https://www.akc.org/expert-advice/dog-breeding/how-long-are-dogs-pregnant/>. (Year: 2012).*
Barreto et al., Decellularlized bovine cotyledons may serve as biological scaffolds with preserved vascular arrangement. Tissue Engineering and Regenerative Medicine, vol. 12, No. 4 (Apr. 2018) e1880-e1888 (Year: 2018).*
Pregnant cows, timing of pregnancy, open cows, pregnancy rate. University of Nebraska, Lincoln [online], 2023 [retrieved on May 12, 2023]. Retrieved from the Internet: <URL: https://beef.unl.edu/faq/pregnant-cows> (Year: 2023).*
Devi et al., Expression and functional role of fibroblast growth factors (FGF) in placenta during different stages of pregnancy in water buffalo (*Bulbalus bubalis*). Theriogenology, vol. 143 (Feb. 2020) pp. 98-112 (Year: 2020).*
Flynn et al., Decellularized placental matrices for adipose tissue engineering. Journal of Biomedical Materials Research, vol. 79A, No. 2 (Nov. 2006) pp. 359-369 (Year: 2006).*
Barreto et al., Mouse placental scaffolds: a three-dimensional environment model for recellularization. Journal of Tissue Engineering. vol. 10 (2019) doi:10.1177/2041731419867962 (Year: 2019).*
Queensberry et al., Breeding and Reproduction of Mice. Merck Manual (2020) (Year: 2020).*
Shakouri-Motlagh et al., The application of decellularized human term fetal membranes in tissue engineering and regenerative medicine (TERM). Placenta, vol. 59 (2017) pp. 124-130 (Year: 2017).*
Badylak et al., "Progress in Tissue Engineering and Regenerative Medicine," Proc Natl Acad Sci USA, 107 (8):3285-3286 (2010).
International Preliminary Report on Patentability for International PCT Application No. PCT/US2018/014742 dated Feb. 1, 2019.
International Search Report and Written Opinion for International PCT Application No. PCT/US2018/014742 dated Mar. 26, 2018.
Quinby, "Plastic and Reconstructive Surgery," 1982, 70, 6, 711-716.
Sheridan et al., "Tissue Engineering: Part C," 2013, 19, 12, 981-990.
Barreto et al., "Decellularized Bovine Cotyledons May Serve as Biological Scaffolds with Preserved Vascular Arrangement," J Tissue Eng Regen Med, 2018, 12, e1880-e1888.
Devi et al., "Expression and Functional Role of Fibroblast Growth Factors (FGF) in Placenta During Different Stages of Pregnancy in Water Buffalo (*Bubalus Bubalis*)," Theriogenology, 143, 2020, 98-112.
Faulk et al., "Human Amnion as an Adjunct in Wound Healing," The Lancet, 1980, 1156-1158.
Favaron et al., "Establishment of 3-Dimensional Scaffolds from Hemochorial Placentas," Placenta, 2019, 81, 32-41.
Fratini et al., "Canine Placenta Recellularized Using Yolk Sac Cells with Vascular Endothelial Growth Factor," BioResearch Open Access, 2018, 7:1, 101-106.
InnovaMatrix 510(k) FDA Pre-market Notification ID K193552 dated Dec. 20, 2019 filed by Triad Life Sciences, Inc.

(Continued)

*Primary Examiner* — Kara D Johnson
(74) *Attorney, Agent, or Firm* — DLA Piper LLP (US)

(57) ABSTRACT

Disclosed herein are methods and compositions of decellularized preterm placental tissue. Compositions comprise decellularized regenerative tissue derived from animal placentas that are harvested preterm, i.e., before the completion of the normal duration of gestation. Preterm placental tissue may contain a high level of growth factors and other beneficial components that aid in tissue regeneration and healing.

15 Claims, 3 Drawing Sheets

(56) References Cited

OTHER PUBLICATIONS

Matias et al., "Optimization of Canine Placenta Decellularization: An Alternative Source of Biological Scaffolds for Regenerative Medicine," Cells Tissues Organs, 2018, 205, 217-225.

Oliveira et al., "Composition and Significance of Glycosaminoglycans in the Uterus and Placenta of Mammals," Braz Arch Biol Technol, 2015, 58:4, 512-520.

Third Party Observation re: International Application No. PCT/US2021/019389 submitted to the International Bureau on Jun. 20, 2022.

Elshenawy et al., "The Metabolic Signature of the Placenta in Spontaneous Preterm Birth," International Journal of Molecular Sciences (Feb. 4, 2020) vol. 21, No. 3, Article 1043, pp. 1-21.

International Search Report and Written Opinion for International PCT Patent Application No. PCT/US2021/019389 dated May 24, 2021.

Schneider et al., "Decellularized human placenta chorion matrix as a favorable source of small-diameter vascular grafts", Acta Biomaterialia, 29, pp. 125-134, Jan. 29, 2016.

Benson-Martin et al., "The Young's modulus of fetal preterm and term amniotic membranes," European Journal of Obstetrics & Gynecology and Reproductive Biology, Elservier Ireland Ltd., IE, vol. 128, No. 1-2, Sep. 1, 2006; pp. 103-107, XP027921135.

Extended European Search Report for EP 21760549.2 dated Mar. 15, 2024 (9 pages).

Leonel et al., "Decellularization of placentas: establishing a protocol," Brazilian Journal of Medical and Biological Research, Dec. 2010, vol. 51, No. 1, Nov. 17, 2017, p. e6382, XP009514687.

Portmann-Lanz et al., "Manufacture of a Cell-free Amnion Matrix Scaffold that Supports Amnion Cell Outgrowth In Vitro," Placenta, WB Saunders GB vol. 28, No. 1, Nov. 17, 2006 pp. 6-13, XP005739883.

\* cited by examiner

A  B

A  B

PLACENTAL TISSUE COMPOSITIONS AND METHODS

CROSS-REFERENCE TO RELATED APPLICATIONS

This application claims priority to and benefit of U.S. Provisional Application No. 62/983,060, filed Feb. 28, 2020, which is incorporated by reference herein in its entirety.

FIELD

The present disclosure relates generally to compositions suitable for use in tissue regeneration and more particularly to compositions comprising decellularized preterm placental tissue.

BACKGROUND

Proper wound healing and recovery from injuries is essential for human health, and as such, regenerative medicine has emerged as a promising strategy for developing functional tissue constructs to reconstruct and restore damaged musculoskeletal tissues or organs (Badylak et al., Proc Natl Acad Sci USA, 107(8):3285-3286 (2010)). One strategy that has been adopted is the use of acellular biomaterials or scaffolds capable of inducing tissue regeneration in vivo, for example, extracellular matrix material derived from mammalian tissues. Some of these mammalian tissues that have been described in patent literature include small intestine submucosa (SIS), liver basement membrane (LBM), urinary bladder submucosa (UBS) and stomach submucosa (SS). See U.S. Pat. Nos. 5,554,389, 4,902,508, and 5,281,422. Tissue regeneration after injury is limited by formation of scar around the lesion site. Despite years of research, the mechanism of scar formation as well as ways to minimize it still remain fundamental questions, since scar tissue blocks the delivery of therapeutic drugs and axonal growth into the injury site, preventing optimization of recovery and regeneration.

Additionally, scar tissue and inflammation pose a barrier in implantation procedures, often resulting in infection, thrombogenesis, scar tissue, or degradation of the implant by the body. There is thus a need to provide compositions and methods that promote tissue regeneration and growth, while at the same time reducing inflammation and scar tissue in the body. Such a composition would represent an improvement in the field of tissue engineering, thereby providing compositions that may be used during or after surgical procedures to promote wound healing and reduce the risk of implant rejection.

SUMMARY

Disclosed herein are methods and compositions of decellularized preterm placental tissue. The disclosure provides decellularized regenerative tissue compositions derived from animal placentas that are harvested preterm, i.e., before the completion of the normal duration of gestation. The present disclosure provides a composition comprising decellularized preterm placental tissue, wherein the preterm placental tissue is obtained from an animal in gestation having at least about 1 week to about 20 weeks remaining in a normal gestation period of the animal. In any embodiment, the decellularized preterm placental tissue may comprise one or more of an amnion layer, a chorion layer, and an allantois layer. In any embodiment, the decellularized preterm placental tissue may advantageously comprise one or more growth factors in an amount that is at least about 120% (e.g., 120% to 300%) of the amount of growth factors present in decellularized placental tissue obtained from a full-term placenta of the same animal. Further, and in any embodiment, the decellularized preterm placental tissue may advantageously comprise one or more extracellular matrix components in an amount that is at least about 120% (e.g., 120% to 300%) of the amount of extracellular matrix components present in decellularized placental tissue obtained from a full-term placenta of the same animal. In any embodiment, the animal is a mammal, such as, but not limited to, bovine, porcine, murine, ovine, equine, canine, caprine, rabbit, primate, and feline.

In any embodiment, the composition may further comprise one or more an active agents selected from an antibiotic, antifungal agent, anti-viral agent, anti-pain agent, anesthetic, analgesic, steroidal anti-inflammatory, non-steroidal anti-inflammatory, anti-neoplastic, anti-spasmodic, hormone, enzyme, enzyme inhibitor, anticoagulant, antithrombic agent, polypeptide, oligonucleotide, polynucleotide, nucleoprotein, compound modulating cell migration, compound modulating proliferation and growth of tissue, and vasodilating agent.

The present disclosure also provides a tissue regenerative scaffold comprising decellularized preterm placental tissue, wherein the preterm placental tissue is obtained from an animal in gestation having at least about 1 week to about 20 weeks remaining in a normal gestation period of the animal. In any embodiment, the decellularized preterm placental tissue may comprise one or more of an amnion layer, a chorion layer, and an allantois layer. In any embodiment, the decellularized preterm placental tissue may advantageously comprise one or more growth factors in an amount that is at least about 120% (e.g., 120% to 300%) of the amount of growth factors present in decellularized placental tissue obtained from a full-term placenta of the same animal. Further, and in any embodiment, the decellularized preterm placental tissue may advantageously comprise one or more extracellular matrix components in an amount that is at least about 120% (e.g., 120% to 300%) of the amount of extracellular matrix components present in decellularized placental tissue obtained from a full-term placenta of the same animal. In any embodiment, the animal is a mammal, such as, but not limited to, bovine, porcine, murine, ovine, equine, canine, caprine, rabbit, primate, and feline.

The present disclosure also provides a method of promoting angiogenesis in a subject, wherein the method comprises administering to the subject in need thereof a composition comprising decellularized preterm placental tissue, wherein the preterm placental tissue is obtained from an animal in gestation having at least about 1 week to about 20 weeks remaining in a normal gestation period of the animal. In any embodiment, the decellularized preterm placental tissue may comprise one or more of an amnion layer, a chorion layer, and an allantois layer. In any embodiment, the decellularized preterm placental tissue may advantageously comprise one or more growth factors in an amount that is at least about 120% (e.g., 120% to 300%) of the amount of growth factors present in decellularized placental tissue obtained from a full-term placenta of the same animal. Further, and in any embodiment, the decellularized preterm placental tissue may advantageously comprise one or more extracellular matrix components in an amount that is at least about 120% (e.g., 120% to 300%) of the amount of extracellular matrix components present in decellularized placental tissue obtained from a full-term placenta of the same animal. In any embodiment, the animal is a mammal, such as, but not limited to, bovine, porcine, murine, ovine, equine, canine, caprine, rabbit, primate, and feline.

The present disclosure also provides a method of treating a wound in a subject, wherein the method comprises administering to the subject in need thereof a composition comprising decellularized preterm placental tissue, wherein the preterm placental tissue is obtained from an animal in gestation having at least about 1 week to about 20 weeks remaining in a normal gestation period of the animal. The decellularized preterm placental tissue may have any of the characteristics listed herein.

The present disclosure also provides a method of stimulating tissue regeneration in a subject, wherein the method comprises administering to the subject in need thereof a composition comprising decellularized preterm placental tissue, wherein the preterm placental tissue is obtained from an animal in gestation having at least about 1 week to about 20 weeks remaining in a normal gestation period of the animal. The decellularized preterm placental tissue may have any of the characteristics listed herein. The decellularized preterm placental tissue can be used to regenerate different tissue types in a subject, including but not limited to, fat, skin, muscular tissue, nervous tissue (central and peripheral nervous system), cardiac tissue, vascular tissue.

DETAILED DESCRIPTION

Figure 1:
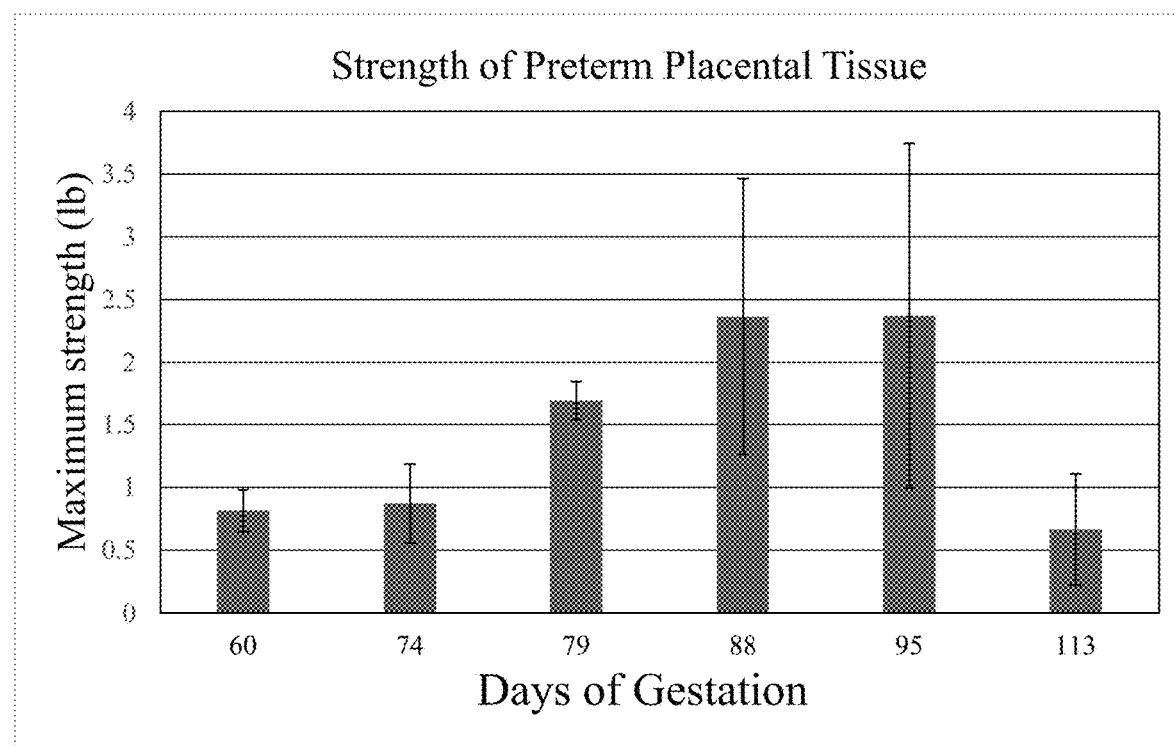
FIG. 1 depicts measured mechanical strength of preterm placental membranes obtained from pigs of different gestational periods.

The present disclosure provides compositions comprising decellularized preterm placental tissue (herein "preterm placental compositions") that may be used in tissue regeneration and advantageously promote angiogenesis and healing of the affected area in need of regeneration. Such preterm placental compositions and methods of their use, as disclosed herein, may be used in surgical procedures, for example, in grafts or in transplant medicine, for example, to reduce inflammation and rejection of a graft or transplant. Specific examples of various preterm placental compositions and methods of their use will be described further herein below.

However, before the present compositions and methods are described, it is to be understood that the scope of the disclosure is not limited to the particular processes, compositions, or methodologies described, as these may vary. It is also to be understood that the terminology used in the description is for the purpose of describing the particular versions or embodiments only, and is not intended to limit the scope of the present disclosure which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the methods and systems disclosed herein, the preferred methods, devices, and materials are now described. Nothing herein is to be construed as an admission that the methods and systems described herein are not entitled to antedate such disclosure by virtue of prior invention.

Definitions

The following explanations of terms and methods are provided to better describe the present disclosure and to guide those of ordinary skill in the art in the practice of the present disclosure.

The singular forms "a," "an," and "the" include plural referents unless the context clearly indicates otherwise. Thus, for example, reference to a "polymer" includes a single polymer as well as two or more of the same or different polymers; reference to an "excipient" includes a single excipient as well as two or more of the same or different excipients.

As used herein, the term "about" when immediately preceding a numerical value means a range of plus or minus 10% of that value (e.g., "about 50" means 45 to 55, "about 25,000" means 22,500 to 27,500), unless the context of the disclosure indicates otherwise, or is inconsistent with such an interpretation.

Unless otherwise defined, all technical and scientific terms used herein have the same meaning as commonly understood to one of ordinary skill in the art. Although methods and materials similar or equivalent to those described herein can be used in the practice or testing of the present disclosure, suitable methods and materials are described below. The materials, methods, and examples are illustrative only and are not intended to be limiting. All references cited herein are incorporated by reference in their entirety.

The terms "administer," "administering," or "administration" as used herein refer to either directly administering decellularized preterm placental tissue or a composition comprising decellularized preterm placental tissue.

The transitional term "comprising," which is synonymous with "including," "containing," or "characterized by," is inclusive or open-ended and does not exclude additional, non-recited elements or method steps. By contrast, the transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. In embodiments or claims where the term comprising is used as the transition phrase, such embodiments can also be envisioned with replacement of the term "comprising" with the terms "consisting of" or "consisting essentially of."

The term "decellularized" as used herein means "having been subjected to a process that removes all or substantially all (e.g., about 80%, about 90%, about 95%, about 96%, about 97%, about 98%, about 99%, or 99.5% of) cellular components and cellular debris from the material described by the word 'decellularized.'" For example, "decellularized placental tissue" may comprise no, or substantially no, cells or cellular debris originating from the organism from which the material (e.g., tissue) was obtained. For example, "decellularized placental tissue" may comprise no more than 20% of cells and cellular debris that were initially present in the placental tissue, which also includes no more than about 15%, no more than about 10%, no more than about 5%, no more than about 4%, no more than about 3%, no more than about 2%, no more than about 1%, or no detectable cells or cellular debris origination from the originating organism. In any embodiment, "decellularized placental tissue" may comprise no, or substantially no, cells or cellular debris of any origin (human or non-human). In any embodiment disclosed herein, decellularized material may be acellular (e.g., contain no detectable cells, human or animal) or substantially acellular (e.g., contain no more than about 20%, no more than about 15%, no more than about 10%, no more than about 5%, no more than about 4%, no more than about 3%, no more than about 2%, or no more than about 1% of detectable human or animal cells).

The term "preterm placental tissue" as used herein refers to placental tissue obtained from healthy animals before they proceed to full-term labor.

The term "patient" and "subject" are interchangeable and may be taken to mean any living organism which may be treated with compositions disclosed herein. As such, the terms "patient" and "subject" may include, but are not limited to, any non-human mammal, primate, or human. A patient or subject may be an adult, child, or infant. In any embodiment of any method disclosed herein, the patient or subject is a human.

As used herein the terms "treat," "treated," or "treating" refer to both therapeutic treatment and prophylactic or preventative measures, wherein the object is to protect against (partially or wholly) or slow down (e.g., lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this application, beneficial or desired clinical results include, but are not limited to, alleviation of symptoms; diminishment of the extent or vigor or rate of development of the condition, disorder or disease; stabilization (e.g., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease. Treatment seeks to elicit a clinically significant response without excessive levels of side effects.

As used herein, placental tissue refers to any tissue derived from a placenta, which may include one or more of a chorion layer, an allantois layer, a yolk sac, an amnion layer, a basal plate (or lamina), and any vasculature/microvasculature. As used herein, a placental membrane refers to a layered structure comprising one or more of a chorion layer, an allantois layer, and an amnion layer.

Human placental membranes, including amnion and chorion layers, have been used as tissue regenerative materials in various medical applications. However, the use of human placenta is limited by the shortage of tissue donors and the high cost of tissue processing. Animal placentas, for example, mammalian placentas such as bovine placentas, are attractive replacements for human placental membranes. To avoid graft rejection of xenographic tissues, the animal placental tissue can be decellularized to eliminate the presence of cells and cellular debris.

Disclosed herein are compositions comprising decellularized preterm animal placental tissue and methods for their use. Decellularized preterm placental tissue may be prepared by subjecting preterm placental tissue to a decellularization process. As used herein, "preterm" refers to a gestational period before the completion of the normal duration of gestation. Preterm placental tissue is preferably obtained from the placenta of a healthy animal in gestation that would otherwise proceed to full-term labor. In contrast, "premature placental tissue" refers to placental tissue obtained after a clinically premature birth. Without wishing to be bound by theory, it is believed that a preterm placenta and a premature placenta may have different biological components due to underlying physiological differences in the gestating animal and the unborn offspring. For example, a preterm placenta may comprise higher growth factor levels, higher mechanical strength, higher levels of glycosaminoglycan, and lower levels of matrix metalloproteinase than a premature placenta. It is believed that preterm placental tissue possesses tissue regenerative properties and therefore may be useful for use as regenerative tissue, for example, as membranes, scaffolds, and devices for tissue regeneration.

Therefore, in one embodiment, the present disclosure provides a composition comprising decellularized preterm placental tissue. Preterm placental tissue may comprise, in any embodiment disclosed herein, one or more of a chorion layer, an allantois layer, and an amnion layer. Preterm placental tissue suitable for use in the compositions and methods disclosed herein may be obtained from an animal, for example a mammal, including, but not limited to, human, bovine, porcine, murine, ovine, equine, canine, caprine, rabbit, primate, and feline. In any embodiment disclosed herein, the preterm placental tissue is obtained from a non-human animal.

In any embodiment disclosed herein, preterm placental tissue may be obtained before the completion of 100% of the natural gestational period, that is, the placental tissue can be obtained when about 95% of the gestational period is complete, about 90% of the gestational period is complete, about 85% of the gestational period is complete, about 80% of the gestational period is complete, about 75% of the gestational period is complete, about 70% of the gestational period is complete, about 65% of the gestational period is complete, about 60% of the gestational period is complete, about 55% of the gestational period is complete, about 50% of the gestational period is complete, about 45% of the gestational period is complete, about 40% of the gestational period is complete, about 35% of the gestational period is complete, about 30% of the gestational period is complete, or any ranges therebetween. In any embodiment disclosed herein, the preterm placental tissue may be obtained from an animal in gestation, having at least about 1 week to about 20 weeks remaining in the normal (i.e., natural or average) gestation period of the animal. For example, preterm placental tissue may be obtained at least about 1 week to about 20 weeks prior to, about 1 week to about 18 weeks prior to, about 1 week to about 16 weeks prior to, about 1 week to about 14 weeks prior to, about 1 week to about 12 weeks prior to, about 1 week to about 10 weeks prior to, or about 1 week to about 5 weeks prior to completion of the normal gestation period of the animal. Specific examples include about 1 week, about 2 weeks, about 3 weeks, about 5 weeks, about 6 weeks, about 8 weeks, about 10 weeks, about 12 weeks, about 15 weeks, or about 20 weeks prior to completion of the normal gestation period of the animal. In any embodiment disclosed herein, preterm placental tissue may be obtained at any time point during the second trimester and early third trimester of an animal.

For example, the length of the natural gestational period in cattle is about 281 days. Bovine preterm placental tissue can be obtained from a cow at about 275 days of gestation, about 270 days of gestation, about 260 days of gestation, about 250 days of gestation, about 240 days of gestation, about 230 days of gestation, about 200 days of gestation, or at any period between about 100 days of gestation and about 275 days of gestation.

In another example, the length of the natural gestational period in horse is about 337 days. An equine preterm placental tissue can be obtained from a horse at about 330 days of gestation, about 320 days of gestation, about 300 days of gestation, about 290 days of gestation, about 280 days of gestation, about 270 days of gestation, about 250 days of gestation, or at any period between about 110 days of gestation and about 330 days of gestation.

In yet another example, the length of the natural gestational period in pigs is about 114 days. A porcine preterm placental tissue can be obtained from a pig at about 110 days of gestation, about 100 days of gestation, about 95 days of gestation, about 90 days of gestation, about 80 days of gestation, about 70 days of gestation, about 60 days of gestation, or at any period between about 50 days of gestation and about 110 days of gestation.

In any embodiment disclosed herein and advantageously, decellularized preterm placental tissue, decellularized as disclosed herein, may comprise growth factors and extracellular matrix components such as collagen (e.g., collagen type I, collagen type II, collagen type III, collagen type IV, collagen type V), hyaluronan, elastin, fibronectin, glycosaminoglycan/s (e.g., chondroitin sulfate, keratin sulfate, dermatan sulfate, heparan sulfate), laminin/s, mucopolysaccharide/s, proteoglycan/s, and the like.

Decellularized preterm placental tissue derived from a preterm placenta may comprise higher growth factor levels than decellularized placental tissue derived from a full-term placenta. For example, in any embodiment disclosed herein, decellularized preterm placental tissue may comprise one or more growth factors in an amount that is at least: about 2% greater, about 5% greater, about 10% greater, about 15% greater, about 20% greater, about 25% greater, about 30% greater, about 50% greater, about 75% greater, about 90% greater, about 100% greater, about 125% greater, about 150% greater, or about 200% greater than the growth factors present in decellularized placental tissue obtained from a full-term placenta of the same animal.

Decellularized preterm placental tissue derived from a preterm placenta may comprise one or more growth factors in an amount that is at least: about 1 fold greater, about 1.5 fold greater, about 2 fold greater, about 2.5 fold greater, about 3 fold greater, about 5 fold greater, about 7 fold greater, or about 10 fold greater than the growth factors present in decellularized placental tissue obtained from a full-term placenta of the same animal. Non-limiting examples of growth factors include platelet-derived growth factor (PDGF), basic fibroblast growth factor (bFGF), epidermal growth factor (EGF), granulocyte-colony stimulating factor (GCSF), placenta growth factor (PIGF), fibroblast growth factor (FGF), transforming growth factor (TGF), insulin-like growth factor (IGF), and combinations thereof. In any embodiment disclosed herein, decellularized preterm placental tissue may comprise basic fibroblast growth factor.

Decellularized preterm placental tissue derived from a preterm placenta may comprise one or more growth factors in an amount from about 1 pg/mg of decellularized preterm placental tissue to about 50000 pg/mg of decellularized preterm placental tissue, about 10 pg/mg of decellularized preterm placental tissue to about 10000 pg/mg of decellularized preterm placental tissue, about 50 pg/mg of decellularized preterm placental tissue to about 5000 pg/mg of decellularized preterm placental tissue, or about 600 pg/mg of decellularized preterm placental tissue to about 800 pg/mg of decellularized preterm placental tissue.

Decellularized preterm placental tissue derived from a preterm placenta may comprise one or more extracellular matrix components in an amount that is at least: about 2% greater, about 5% greater, about 10% greater, about 15% greater, about 20% greater, about 25% greater, or about 30% greater than the extracellular matrix components present in decellularized placental tissue obtained at full term of the same animal. For example, decellularized preterm placental tissue may comprise one or more extracellular matrix components in an amount that is at least: about 1 fold greater, about 1.5 fold greater, about 2 fold greater, about 2.5 fold greater, about 3 fold greater, about 5 fold greater, about 7 fold greater, or about 10 fold greater than the extracellular matrix components present in decellularized placental tissue obtained from a full-term placenta of the same animal. Non-limiting examples of extracellular matrix components include collagen, hyaluronan, elastin, fibronectin, chondroitin sulfate, keratin sulfate, dermatan sulfate, heparan sulfate, laminin/s, mucopolysaccharide/s, proteoglycan/s, and any combination thereof. In any embodiment disclosed herein, decellularized preterm placental tissue may comprise hyaluronic acid.

In any embodiment disclosed herein, a preterm placental composition may comprise decellularized preterm placental tissue, which, in turn, comprises decellularized preterm placental membrane. In any embodiment disclosed herein, a composition may comprise decellularized preterm placental membrane that is subsequently separated into one or more of its constituent amnion layers, chorion layers, and allantois layers. In any embodiment, a preterm placental composition, as described herein, may be formed into any shape, such as but not limited to, sheet, sponge, foam, film, tube, granulate, powder, injectable, or gel. For example, a preterm placental composition may be formed into a hydrogel. In another example, a preterm placental tissue can be decellularized, minced, and dried (air dried or freeze dried) to form granulated powder. Therefore, the present disclosure provides a sheet, sponge, foam, film, tube, granulate, injectable, powder, or gel composition comprising a preterm placental composition, optionally dried, as disclosed herein, comprising decellularized preterm placental tissue.

In any embodiment disclosed herein, a preterm placental composition, as described herein, may further include one or more active agents, such as an antibiotic, antifungal agent, anti-viral agent, anti-pain agent, anesthetic, analgesic, steroidal anti-inflammatory, non-steroidal anti-inflammatory, anti-neoplastic, anti-spasmodic, hormone, growth factor, protein, enzyme, enzyme inhibitor, anticoagulant, antithrombic agent, polypeptide, oligonucleotide, polynucleotide, nucleoprotein, compound modulating cell migration, compound modulating proliferation and growth of tissue, or vasodilating agent.

For example, in any embodiment disclosed herein, a preterm placental composition may additionally comprise one or more of atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oxytetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, insulin, verteporfin, pegaptanib, ranibizumab, one or more antineoplastics, one or more caspase-1 inhibitors, one or more caspase-3 inhibitors, α-adrenoceptors agonists, and one or more NMDA antagonists, and any combination thereof.

In any embodiment disclosed herein, a preterm placental composition may, for example, comprise one or more active agents belonging to Class I-Class V antiarrhythmic agents, such as (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem; and (Class V) adenosine, and digoxin, and any combination thereof.

Alternatively, in any embodiment disclosed herein, a preterm placental composition may comprise one or more antibiotics, such as an aminoglycoside, a cephalosporin, chloramphenicol, clindamycin, an erythromycin, a fluoroquinolone, a macrolide, an azolide, metronidazole, penicillin, a tetracycline, trimethoprim-sulfamethoxazole, or vancomycin.

Alternatively, in any embodiment disclosed herein, a preterm placental composition may comprise one or more steroids, such as an andrane (e.g., testosterone), a cholestane, a cholic acid, a corticosteroid (e.g., dexamethasone), an estrane (e.g., estradiol) a pregnane (e.g., progesterone), and any combination thereof.

Alternatively, in any embodiment disclosed herein, a preterm placental composition may comprise one or more narcotic analgesics, such as morphine, codeine, heroin, hydromorphone, levorphanol, meperidine, methadone, oxycodone, propoxyphene, fentanyl, methadone, naloxone, buprenorphine, butorphanol, nalbuphine, pentazocine, and any combination thereof.

Alternatively, in any embodiment disclosed herein, a preterm placental composition may comprise one or more chemotherapy agents, such as an antimetabolite (e.g., purine analogs, pyrimidine analogues, antifolates), a plant alkaloid (e.g., vincristine, vinblastine, vinorelbine, vindesine, podophyllotoxin, etoposide, and teniposide), a taxane (e.g., paclitaxel and docetaxel), a topoisomerase inhibitor (e.g., irinotecan, topotecan, amsacrine, etoposide, etoposide phosphate and teniposide), a cytotoxic antibiotic (e.g., actinomycin, bleomycin, plicamycin, mytomycin), an anthracycline (e.g., doxorubicin, daunorubicin, valrubicin, idarubicin, epirubicin), or an antibody treatment (e.g., abciximab, adamlimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, ipilimumab, muromonab-CD3, natalizumab, ofatumumab, omalizumab, palivizumab, panitumumab, ranibizumab, rituximab, tocilizumab (atlizumab), tositumomab, trastuzumab, and any combination thereof.

Alternatively, in any embodiment disclosed herein, a preterm placental composition may comprise one or more anti-inflammatory agents, such as alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, zomepirac sodium, and any combination thereof.

Alternatively, in any embodiment disclosed herein, a preterm placental composition may comprise one or more biocompatible excipients such as, but not limited to, ceramics, bioglass, calcium sulfate, demineralized bone matrix, coral, calcium phosphates, hydroxyapatite, tricalcium phosphate, collagen/ceramic composite, PCL, PLLA, PLGA, PEG, PGA, alginates, silk, dextran gelatin, agarose, chitosan, propylene glycol alginate, chitin, biotin, avidin, solubilized basement membrane (e.g., MATRIGEL®), polyethylene glycol, glycerol, poly(methyl methacrylate), polyurethane, acryloylmorpholine, N,N-dimethyl acrylamide, N-vinyl pyrrolidone and tetrahydrofurfuryl methacrylate, hydroxyapatite, cross-linked or functionalized hyaluronan-based collagen and alginate, polyurethane, polylactic acid, or any combination thereof. In any embodiment disclosed herein, a composition of decellularized preterm placental tissue may further comprise one or more salts of calcium, barium, aluminum, strontium, copper, zinc, magnesium, manganese, cobalt, iron, or any combination thereof.

A preterm placental composition, as disclosed herein, may be immunocompatible. Immunocompatability of preterm placental tissue can be achieved by any selective depletion step that removes immunogenic cells or factors or immunogenicity from the placenta or placental derived tissue. For example, preterm placental tissue may be devoid of one or more surface antigens that are involved in tissue rejection, such as, but not limited to, HLA-A, HLA-B, HLA-C, and β2-microglobulin.

Alternatively and in any embodiment disclosed herein, decellularized preterm placental tissue or a composition thereof may further comprise one or more cells, for example, human cells such as, but not limited to, embryonic stem cells, mesenchymal stem cells, progenitor cells, hematopoietic stem cells, other tissue specific stem cells, induced pluripotent stem cells, endothelial cells, smooth muscle cells, cardiomyocyte, fibroblasts, beta cells, white blood cells, macrophage, neurons, Schwann cells, chondrocytes, satellite cells. The cells can be seeded on a decellularized preterm placental composition. The cells may be seeded on the surface of a preterm placental composition, or inside the porous structure of a preterm placental composition. In another example, the cells can be encapsulated in a cavity formed by a preterm placental composition. For example, a pouch can be made from preterm placental membranes, and cells can be placed inside the pouch.

Methods of Preparation

The present disclosure provides a method for preparing a preterm placental composition comprising a) obtaining preterm placental tissue from an animal; and b) decellularizing the preterm placental tissue to generate decellularized preterm placental tissue.

According to the methods disclosed herein, after obtaining preterm placental tissue, the preterm placental tissue may be decellularized to remove cellular components and cellular debris therefrom. Decellularization may be performed in accordance with any method known in the art. For example, in any embodiment disclosed herein, preterm placental tissue may be decellularized by a process comprising exposing preterm placental tissue to a hypertonic solution followed by a hypotonic solution, and repeating the alternating treatments as many times as necessary to effect sufficient cellular disruption. For example, preterm placental tissue may be rinsed with hypotonic distilled water followed by hypertonic 1M saline, alternating between the two solutions to achieve sufficient cellular disruption. The preterm placental tissue may be further rinsed in a buffered solution (e.g., PBS, Tris buffer, and the like).

In another example, and in any embodiment disclosed herein, decellularization of preterm placental tissue may be performed by repeatedly freezing and thawing the preterm placental tissue and further washing the preterm placental tissue in PBS or water. Other methods include treating preterm placental tissue with 0.01% to 5% of an acid (e.g., peracetic acid, acetic acid, deoxycholic acid, or the like). Further methods include treating preterm placental tissue with detergents, such as anionic detergents comprising bile acid salts and/or sodium dodecyl sulfate (SDS), cationic detergents comprising cetyl trimethyl-ammonium bromide (CTAB), and non-ionic or zwitterionic detergents (e.g., BRLJ®, TRITON®, or CHAPS). A detergent may be used at a concentration of about 0.1% to about 0.5%, about 0.1%, to about 1%, or about 0.1% to about 2%, as well as any values between these ranges. Preterm placental tissues may be contacted with detergents for a period of about 1 day, about 2 days, about 3 days, about 4 days, about 5 days, about 6 days, about 7 days, or about 10 days. For example, placental tissue may be contacted with about 0.5% SDS for about 5 days during a decellularization process.

In another example, and in any embodiment disclosed herein, decellularization of preterm placental tissue may be performed by treating the placental tissue with one or more biological enzymes, such as trypsin, thermolysin, collagenase, metalloproteinase, dispase, hyaluronidase, papain, pepsin, elastase, pronase, DNase, endonucleases, and the like.

Optionally and in any embodiment disclosed herein, preterm placental tissue may be decontaminated or sterilized. Sterilization and/or decontamination may be carried out before or after the decellularization step. In some embodiments, preterm placental tissue is decontaminated or sterilized before the decellularization step. In some embodiments, preterm placental tissue is decontaminated or sterilized after the decellularization step. Decontamination may be performed by contacting decellularized preterm placental tissue with a suitable disinfectant, such as ethanol, peracetic acid, or an antibiotic. Contacting may be carried out for a period of at least about 15 minutes, about 20 minutes, about 30 minutes, about 45 minutes, or about 60 minutes. Preterm placental tissue may undergo a decontamination process such that the bioburden is reduced in the preterm placental tissue to undetectable levels (i.e., below the threshold of detection by an assay that detects microbial presence), while also reducing damage or loss of endogenous matrix components and bioactive factors. In some embodiments, the bioburden is reduced to zero. Preterm placental tissue may undergo a sterilization process, such as sterilization with ethylene oxide, electron beam sterilization, and/or sterilization via gamma irradiation.

In any embodiment disclosed herein, a preterm placental composition comprises one or more decellularized placental components such as decellularized placental membrane or any decellularized layer thereof, such as decellularized chorion, decellularized allantois, and decellularized amnion. For example, preterm placental tissue may be decellularized without processing to separate one or more of the placental membranes or layers thereof, such as the amnion, chorion, or allantois.

Alternatively, in any embodiment disclosed herein, a preterm placental composition may not comprise all components of preterm placental tissue. For example, preterm placental tissue may be processed to separate placental membrane from other placental components or one or more layers of the placental membrane, such as the chorion layer, the allantois layer, and the amnion layer, from other placental components, thereby producing the preterm placental tissue which is subsequently incorporated into a preterm placental composition, as disclosed herein.

Separation may be done by any effective method, for example, by subjecting preterm placental tissue to a saline bath, followed by isolating the placental membrane from other placental components, or one or more of the amnion layers, chorion layers, and allantois layers from each other and other placental components. Separation can also be performed by mechanical dissection and peeling. Separation may be performed before or after decellularization.

For example, in embodiments where separation is carried out before decellularization, at least one of the separated parts (e.g., placental membrane or one or more of the amnion layers, chorion layers, and allantois layers) is subsequently decellularized. In any embodiment disclosed herein, any layer or layers may be removed intact and further processed, for example, decellularized to produce additional decellularized preterm placental tissue that may be incorporated into the same or a different preterm placental composition, as disclosed herein.

In embodiments where separation is carried out after decellularization, preterm placental tissue may be decellularized, followed by subsequent separation of the placental membrane or one or more layers thereof, such as the chorion layer, the allantois layer, and the amnion layer. Alternatively, a placental membrane may be separated from preterm placental tissue prior to decellularization, after which the placental membrane is decellularized, followed by subsequent and optional separation of one or more of the chorion layer, the allantois layer, and the amnion layers. In such embodiments, a preterm placental composition may comprise decellularized preterm placental tissue comprising one or more of a decellularized preterm placental membrane, a decellularized chorion layer, a decellularized allantois layer, and a decellularized amnion layer.

In any embodiment disclosed herein, decellularized preterm placental tissue may be processed into a preterm placental composition taking any form or shape, such as, but not limited to, sheet, sponge, foam, film, granulate, tube, powder, injectable, or gel. For example, decellularized preterm placental tissue may be incorporated into a hydrogel.

Decellularized preterm placental tissue, obtained by the methods disclosed herein, may be subjected to freeze-drying. While not wishing to be bound by theory, it is believed that the resulting lyophilized placental tissue may exhibit superior physical characteristics, such as flexibility, durability, and softness, while retaining the biologic activities of various components therein, such as growth factors and extracellular matrix components. One of skill in the art is familiar with various freeze-drying techniques, of which any may be used. For example, a cryoprotective substance (cryoprotector) may be used. Non-limiting examples of cryoprotective substances include, but are not limited to, dimethyl sulfoxide (DMSO), glycerol, 1,2-propanediol, 2,3-butanediol, polyethylene glycol, polyvinylpyrrolidone, hydroxyl starch, trehalose, raffinose, sucrose, mannitol, lactose, glucose, maltose, maltotriose, maltotetraose, maltopentaose, maltoheptaose, and combinations thereof.

Advantageously, preterm placental tissue, decellularized and processed as disclosed herein, may retain various components of the endogenous placenta, such as growth factors and extracellular matrix components such as collagen (e.g., collagen type I, collagen type II, collagen type III, collagen type IV, collagen type V), hyaluronan, elastin, fibronectin, glycosaminoglycan/s (e.g., chondroitin sulfate, keratin sulfate, dermatan sulfate, heparan sulfate), laminin/s, mucopolysaccharide/s, proteoglycan/s, and the like.

Decellularized preterm placental tissue composition may be immunocompatible. Immunocompatability of decellularized preterm placental tissue can be achieved by any selective depletion step that removes immunogenic cells or factors or immunogenicity from the placenta or placenta-derived tissue. For example, decellularized preterm placental tissue may rendered immunocompatible by selectively depleting one or more surface antigens that are involved in tissue rejection, such as, but not limited to, HLA-A, HLA-B, HLA-C, and β2-microglobulin.

In any embodiment disclosed herein, a method of making a preterm placental composition, as described herein, may comprise incorporating one or more active agents, such as one or more of an antibiotic, antifungal agent, anti-viral agent, anti-pain agent, anesthetic, analgesic, steroidal anti-inflammatory, non-steroidal anti-inflammatory, antineoplastic, anti-spasmodic, hormone, enzyme, enzyme inhibitor, anticoagulant, antithrombic agent, polypeptides, oligonucleotide, polynucleotide, nucleoprotein, compounds modulating cell migration, a compound modulating proliferation and growth of tissue, a vasodilating agent, or any combination thereof. Specific examples include any and all listed herein.

In any embodiment disclosed herein, a method of making a preterm placental composition, as described herein, may comprise incorporating one or more biocompatible excipients such as a ceramic, bioglass, calcium sulfate, demineralized bone matrix, coral, calcium phosphate, hydroxyapatite, tricalcium phosphate, collagen/ceramic composite, PCL, PLLA, PLGA, PEG, PGA, alginates, silk, dextran gelatin, agarose, chitosan, propylene glycol alginate, chitin, biotin, avidin, solubilized basement membrane (e.g., MATRIGEL®), polyethylene glycol, glycerol, poly(methyl methacrylate), polyurethane, acryloylmorpholine, N,N-dimethyl acrylamide, N-vinyl pyrrolidone and tetrahydrofurfuryl methacrylate, hydroxyapatite, cross-linked or functionalized hyaluronan-based collagen and alginate, polyurethane, polylactic acid, or any combination thereof. Additionally and optionally, one or more salts of calcium, barium, aluminum, strontium, copper, zinc, magnesium, manganese, cobalt, iron, or any combination thereof may be incorporated into a preterm placental composition.

Optionally and in any embodiment disclosed herein, cells may be added to a decellularized preterm placental composition. Cells may be, for example, mammalian cells such as bovine, porcine, murine, ovine, equine, canine, caprine, rabbit, primate, feline, or human cells. In many embodiments, the cells are human cells. Examples of suitable cells include, but are not limited to, embryonic stem cells, mesenchymal stem cells, progenitor cells, hematopoietic stem cells, other tissue specific stem cells, induced pluripotent stem cells, endothelial cells, smooth muscle cells, cardiomyocyte, fibroblasts, beta cells, white blood cells, macrophage, neurons, Schwann cells, chondrocytes, and satellite cells. Cells can be seeded on an acellular decellularized preterm placental composition, such as on the surface of a preterm placental composition or inside the porous structure of a preterm placental composition. In another example, the cells can be encapsulated in a cavity formed by a preterm placental composition. For example, a pouch can be made from preterm placental membranes, and cells can be placed inside the pouch. It is optional to expand or grow the cells in vitro before using the composition. In any embodiment, the cells may be allogenic or autologous to the organism in which the tissue regenerative scaffold will be used.

In any embodiment disclosed herein, any of the various disclosed preterm placental compositions may be utilized in a tissue graft, an engineered tissue scaffold, a biological dressing, a patch graft, any combination thereof, and the like. A tissue graft comprising a preterm placental composition, as described herein, may be provided in a particular shape including, but not limited to, a sheet, tube, a rod, a fragment, or a wedge. For example, a preterm placental composition may be formed into a tissue graft shaped into single or multi-layered sheets useful for wound healing on a skin surface or for attaching to the surface of an internal organ (e.g., heart, stomach, and the like). In another example, a preterm placental composition may be formed into a tissue graft shaped into a sheet may be used to repair or seal a blood vessel. Further, multilayered sheets may be used for tissue reinforcement, such as a hernia patch, breast reconstruction, and the like. A preterm placental composition may be formed into a tissue graft shaped into a sheet, and may also be used as a leak prevention device or as adhesion device. In another example, a preterm placental composition may be formed into a tissue graft rolled into a tube useful as a blood vessel graft (e.g., arterial or venous graft). In yet another example, a preterm placental composition may be formed into a tissue graft rolled into a spiral or tube and used as nerve graft for peripheral nerve repair.

Alternatively, any of the various disclosed preterm placental compositions may be provided in powder or particulate form, which may be useful, for example, in wound healing or drug delivery. Such a preterm placental composition may comprise any of the active agents disclosed herein.

Alternatively, any of the various disclosed preterm placental compositions may be rolled or folded and used as a 3D space filling device, for example, to fill normal or diseased body cavities (e.g., fistula tract, left atrial appendage).

In any embodiment, any of the various disclosed preterm placental compositions may further comprise a mesh construct, wherein the decellularized preterm placental tissue is interwoven into the mesh construct, present in a compartment of the mesh construct, attached to the top of the mesh construct, attached to the bottom of the mesh construct, or attached to both the top and bottom of the mesh construct. A mesh construct can be a mesh biologic (e.g., a biomesh) comprising an organic biomaterial (e.g., porcine dermis, porcine small intestine submucosa, bovine dermis or pericardium, the dermis or fascia lata of a cadaveric human), which may be processed to generate substantially acellular or acellular porous extracellular matrix scaffolds comprising collagen and elastin. As described above, growth factors may remain within the decellularized preterm placental tissue, which may attract endothelial cells and subsequent fibroblasts into the mesh. Alternatively, a mesh construct can also be a synthetic mesh. A mesh construct can be a biocompatible fabric. The fabric can be, for example, polymers of polyethylene, polypropylene, polyester (e.g., polyethylene terephthalate), polyether ether ketone, polyacetal, polyurethane, polytetrafluoroethylene, polycarbonate, polysulfone, polyimide, copolymers thereof, or any combination thereof.

Any of the preterm placental compositions disclosed herein may be manufactured into a tissue regenerative scaffold. The scaffold may be biocompatible with cells, and may allow cells to adhere, function normally, and migrate through the surface and into the structure of the scaffold. The cells may be, for example, mammalian cells such as bovine, porcine, murine, ovine, equine, canine, caprine, rabbit, primate, feline, or human. In many embodiments, the cells are human cells. Scaffolds may also be biodegradable within the body, which may allow the body's cells to eventually replace the foreign scaffold with extracellular components appropriate to the specific local cell types. In any embodiment, the cells may be allogenic or autologous to the organism in which the tissue regenerative scaffold will be used.

Alternatively, any of the various preterm placental compositions may be incorporated into an engineered tissue scaffold. Engineered tissue scaffolds may comprise biodegradable or non-biodegradable natural or synthetic materials such as, but not limited to, polyesters, nylon, polyurethane, polylactic acid (PLA), polyglycolic acid (PGA), polycaprolactone (PCL), polystyrene, poly-1-lactic acid (PLLA), poly-dl-lactic-co-glycolic acid (PLGA), polyvinyl acetate (PVA), polyvinyl chloride (PVC), polyethylene glycol (PEG), polystyrene, and any combination thereof. In any embodiment where the preterm placental composition is incorporated into an engineered tissue scaffold, the tissue scaffold may have a three-dimensional shape that is stable under mechanical stress, for example, by selecting scaffold materials having particular desirable biomechanical properties. Thus, depending on the intended use, a tissue scaffold comprising decellularized preterm placental tissue may be rigid, elastic, resilient, and/or viscoelastic. In some embodiments, the scaffold materials may be selected to form a tissue scaffold having a stiffness that is substantially similar to that of the tissue at the target location. Further, in some embodiments, the tissue scaffold may also resist migration from the target location.

Alternatively, any preterm placental composition disclosed herein may be incorporated into an encasement structure configured to receive a medical device therein. The encasement structure may be of any various shape or size, such as a pouch, a bag, a covering, a shell, a skin, a receptacle, and the like, to accommodate virtually all shapes and sizes of medical devices. Non-limiting examples of medical devices and associated components include, without limitation, a pacemaker, defibrillator, synthetic heart valve, ventricular assist device, artificial heart, physiological sensor, catheter, cardiovascular implantable electronic device (CIED), biosensors, and the electrical leads and lines associated therewith. In any embodiment, any of the various preterm placental compositions disclosed herein may be incorporated into a pouch (with suture or adhesive, which is optionally biodegradable) or an encasement device for medical devices, such as a CIED, or a biosensor. In any embodiment disclosed herein, a preterm placental composition may be incorporated into a cover for a medical device, thereby improving its tissue interface. Examples of such uses include, but are not limited to, the covering of stents, stent grafts, or other implantable devices. In another example, a preterm placental composition may be used as an encasement or covering device for live cells.

Methods of Use

Any of the various preterm placental compositions, as described herein, may be useful in treating a subject. Therefore, the present disclosure provides a method of treating an injury in a subject, augmenting tissue healing in a subject, regenerating tissue in a subject, or any combination thereof. For example, in any embodiment disclosed herein a method may comprise administering to a subject in need thereof a composition comprising decellularized preterm placental tissue, wherein the preterm placental tissue is as described herein. For example, preterm placental tissue may be obtained from an animal having at least about 1 week to about 20 weeks remaining in the normal gestation period of the animal.

Examples of injuries that may be treated using a preterm placental composition, as disclosed herein, include musculoskeletal injuries, such as a connective tissue injury, a cartilaginous tissue injury, a fibrous tissue injury, a muscle tissue injury, a skeletal tissue injury, or any combinations thereof. The musculoskeletal injury can be an injury to tendon, cartilage, ligament, connective tissue, muscle, joint, intervertebral disk, bone, or any combination thereof.

Any of the various preterm placental compositions, as disclosed herein, may be used to treat a musculoskeletal tissue injury or a degenerative condition in a patient. Examples of tissues that may be treated, repaired, regenerated, and/or restored using any of the various preterm placental compositions disclosed herein include, but are not limited to, ligaments, joints, connective tissue, cartilage, intervertebral disk, bone, anterior cruciate ligament, posterior cruciate ligament, medial collateral ligament, lateral collateral ligament, popliteofibular ligament, posterolateral corner, patellar tendon, quadriceps tendon, medial or lateral meniscus, medial or lateral patellofemoral ligament, anterolateral ligament, rotator cuff tendon, glenoid labrum, subscapularis tendon, biceps tendon, coracoclavicular ligaments, anterior talofibular ligament, calcaneofibular ligament, spring ligament, posterior tibialis, anterior tibialis, tendon grafts, extensor and flexor tendons of the hand, foot, upper and lower extremities, intervertebral disk material, muscle tissue including but not limited to, the hamstring muscles, quadriceps, gastrocnemius, soleus, adductors, abductors, hip external and internal rotators, flexors, wrist, elbow and hand extensors, flexors, and other tendons and muscles throughout the musculoskeletal system.

In any embodiment disclosed herein, administering a preterm placental composition, as described herein, to a subject having an injury may promote angiogenesis at the site of the injury. Therefore, the present disclosure provides a method of increasing angiogenesis at the site of an injury in a subject comprising administering to the subject at the site of injury a composition comprising decellularized preterm placental tissue, wherein the preterm placental tissue is obtained from an animal at least about 1 week to about 20 weeks before completion of the normal gestation period of the animal. While not wishing to be bound by theory, it is believed that preterm placental tissue may promote the upregulation or secretion of angiogenic promoting growth factors such as vascular endothelial growth factor (VEGF) and basic fibroblast growth factor (bFGF).

The various preterm placental compositions, as disclosed herein, may be useful in preventing or reducing the formation of scar tissue in a subject. Therefore, the present disclosure provides a method of preventing or reducing formation of scar at a site of injury in a subject comprising administering to the site of injury in the subject a composition comprising decellularized preterm placental tissue, wherein the preterm placental tissue is obtained from an animal having at least about 1 week to about 20 weeks remaining in the normal gestation period of the animal The present disclosure provides a method of treating a wound in a subject comprising administering to the subject at the site of the wound, a composition comprising decellularized preterm placental tissue, wherein the preterm placental tissue is obtained from an animal at least about 1 week to about 20 weeks before completion of the normal gestation period of the animal. Examples of wounds that may be treated using any of the various preterm placental compositions, as disclosed herein, include, but are not limited to lacerations, scrapes, thermal or chemical burns, incisions, punctures, or wounds caused by a projectile. A wound may be an epidermal wound, a skin wound, a chronic wound, an acute wound, an external wound, an internal wound, an ocular wound, a congenital wound, an ulcer, or a pressure ulcer. In any embodiment disclosed herein, the wound may be a tunnel wound, caused by, for example, infection, prolonged inflammation, pressure or shear forces concentrated where tissue layers meet, inadequate drainage absorption due to insufficient wound packing, or degradation of newly granulated tissue due to excessive wound packing. Such wounds may be accidental or deliberate (e.g., wounds caused during or as an adjunct to a surgical procedure).

Non-limiting examples of wound sites to which the various preterm placental compositions, as disclosed herein, may be applied include those that are surgically induced or associated with surgery involving the spine (e.g., spinal fusions), reconstructive surgery, laminectomy, knee, shoulder, or child birth, trauma related wounds or injuries, cardiovascular procedures, angiogenesis stimulation, brain/neurological procedures, hernia repair, tendon repair, bladder repair, and ophthalmic procedures. Such preterm placental compositions may also be applied to wounds or injuries associated with other indications, including, but not limited to, osteoarthritis, inflammatory conditions (e.g., tennis elbow), bone defects, bone repair, and connective tissue repair. For example, optionally, the various preterm placental compositions, as disclosed herein, may be used to treat a wound site associated with surgery of the spine. Any of the various preterm placental compositions, as disclosed herein, may shorten time to wound closure and improve wound healing percentage, for example, by redirecting chronic, non-healing wounds into a healing pattern by promoting cell in-migration, proliferation, and differentiation, along with anti-inflammatory action and antimicrobial action.

Any of the various preterm placental compositions, as disclosed herein, may be useful in stimulating tissue regeneration in a subject. Therefore, the present disclosure provides a method of stimulating tissue regeneration in a subject in need thereof comprising administering to the subject at the site in need of tissue regeneration a composition comprising decellularized preterm placental tissue, wherein the preterm placental tissue is obtained from an animal in gestation having at least about 1 week to about 20 weeks remaining in the normal gestation period of the animal. Tissue regeneration may occur directly or indirectly by the application of any of the various preterm placental compositions, as described herein. For example, tissue regeneration may be effected directly in a wound, injury or defect. While not wishing to be bound by theory, tissue regeneration may also include indirect regeneration of tissue by stimulating expression of therapeutic factors that, in turn, stimulate the production of new tissue. Tissue regeneration may occur at, around, or in the site of a wound or tissue injury. Examples of tissue that may be regenerated using any of the various preterm placental compositions disclosed herein include cardiac tissue, skin tissue, nerve tissue, muscle tissue, fat tissue, musculoskeletal tissue, connective tissue, and combinations thereof. For example, in any embodiment disclosed herein, a method as disclosed herein, for example treating a wound, or inducing tissue regeneration or angiogenesis, may further include carrying out a surgical procedure selected from the group consisting of a tissue graft procedure, tendon surgery, ligament surgery, bone surgery, and spinal surgery. In such applications, any of the various preterm placental compositions disclosed herein and thus used may directly or indirectly stimulate tissue regeneration.

For example, a method of minimizing damage to the cardiovascular system caused by a myocardial infarction in a subject may comprise administering to a cardiac area in the subject a composition comprising decellularized preterm placental tissue, wherein the preterm placental tissue is obtained from an animal in gestation having at least about 1 week to about 20 weeks remaining in the normal gestation period of the animal.

Tissue scaffolds made from decellularized preterm placental tissue can be used for treatment of numerous different anatomical sites and can be used in a wide array of applications. Certain exemplary applications include, but are not limited to, absorptive dressings, dermal regeneration (e.g., for treatments of all types of ulcers and burns), nerve regeneration, cartilage regeneration, connective tissue regeneration or repair, bone regeneration, wound/foam lining, integrated bandage dressings, substrate/base for skin grafts, vascular regeneration, cosmetic surgery, metal and/or polymer implant coating (for example, to increase implant integration and biocompatibility), and replacement of lost tissue (e.g., after trauma, breast reduction, mastectomy, lumpectomy, parotidectomy, or tumor excision).

In any embodiment disclosed herein, a method of treating a subject with a preterm placental composition may comprise applying the composition to the epidermis to accelerate healing associated with a dermal ablation procedure or a dermal abrasion procedure (e.g., including laser ablation, thermal ablation, electric ablation, deep dermal ablation, sub-dermal ablation, fractional ablation, and microdermal abrasion). Other pathologies that may be treated with compositions comprising decellularized preterm placental tissue, as described herein, include traumatic wounds (e.g., civilian and military wounds), surgical scars and wounds, spinal cord injury, avascular necrosis, ablations, and ischemia.

Any of the various preterm placental compositions, as described herein, can be administered topically, including to an internal tissue where access is gained by a surgical procedure. Alternatively, any of the various preterm placental compositions may be manufactured for injection, e.g., through a syringe or needle, or applied as an implant. In various embodiments, a preterm placental composition, as disclosed herein, may be administered as a dermatologically acceptable pharmaceutical product.

EMBODIMENTS

In one embodiment, the present invention includes a composition comprising decellularized preterm placental tissue, wherein the preterm placental tissue is obtained from an animal in gestation having at least about 1 week to about 20 weeks remaining in a normal gestation period of the animal. This embodiment may be combined in combination with one or more of the following elements: Element 1: The composition, wherein the decellularized preterm placental tissue comprises one or more of an amnion layer, a chorion layer, and an allantois layer; Element 2: The composition, wherein the decellularized preterm placental tissue is acellular; Element 3: The composition, further comprising one or more cells; Element 4: Element 3, wherein the cells are selected from the group consisting of embryonic stem cells, mesenchymal stem cells, progenitor cells, hematopoietic stem cells, other tissue specific stem cells, induced pluripotent stem cells, endothelial cells, smooth muscle cells, cardiomyocyte, fibroblasts, beta cells, white blood cells, macrophage, neurons, Schwann cells, chondrocytes, satellite cells, and combinations thereof; Element 5: Element 3 or Element 4, wherein the cells are human cells; Element 6: The composition, wherein the decellularized preterm placental tissue comprises one or more growth factors in an amount at least about at least about 120% of the amount of growth factors present in decellularized placental tissue obtained from a full-term placenta of the same animal; Element 7: The composition, wherein the decellularized preterm placental tissue comprises one or more extracellular matrix components in an amount that is at least about 120% of the amount of extracellular matrix components present in decellularized placental tissue obtained from a full-term placenta of the same animal; Element 8: The composition, wherein the animal is a mammal; Element 9: Element 8, wherein the mammal is selected from the group consisting of bovine, porcine, murine, ovine, equine, canine, caprine, rabbit, primate, and feline; and Element 10: The composition, wherein the composition further comprises one or more an active agent selected from the group consisting of an antibiotic, antifungal agent, anti-viral agent, anti-pain agent, anesthetic, analgesic, steroidal anti-inflammatory, non-steroidal anti-inflammatory, anti-neoplastic, anti-spasmodic, hormone, enzyme, enzyme inhibitor, anticoagulant, anti-thrombic agent, polypeptide, oligonucleotide, polynucleotide, nucleoprotein, compound modulating cell migration, compound modulating proliferation and growth of tissue, and vasodilating agent. The embodiment may be combined in combination with one or more of any element listed above. Specific combinations include Element 1 in combination with one or more of Elements 1-10; Element 2 in combination with one or more of Elements 3-10; Element 3 in combination with one or more of Elements 4-10; Element 6 in combination with one or more of Elements 7-10; Element 7 in combination with one or more of Elements 8-10; and Element 8 with one or both of Elements 9 and 10.

In another embodiment, the present invention includes a scaffold comprising decellularized preterm placental tissue, wherein the preterm placental tissue is obtained from an animal in gestation having at least about 1 week to about 20 weeks remaining in a normal gestation period of the animal. This embodiment may be combined in combination with one or more of the following elements: Element 11: The scaffold, wherein the decellularized preterm placental tissue comprises one or more of an amnion layer, a chorion layer, and an allantois layer; Element 12: The scaffold, wherein the decellularized preterm placental tissue is acellular; Element 13: The scaffold, further comprising one or more cells; Element 13: Element 12, wherein the cells are selected from the group consisting of embryonic stem cells, mesenchymal stem cells, progenitor cells, hematopoietic stem cells, other tissue specific stem cells, induced pluripotent stem cells, endothelial cells, smooth muscle cells, cardiomyocyte, fibroblasts, beta cells, and combinations thereof; Element 14: Element 12 or Element 13, wherein the cells are human cells; Element 15: The scaffold, wherein the animal is a mammal; Element 16: Element 15, wherein the mammal is selected from the group consisting of bovine, porcine, murine, ovine, equine, canine, caprine, rabbit, primate, and feline. This embodiment may be combined in combination with one or more of any element listed above. Specific combinations include Element 11 in combination with one or more of Elements 12-16; Element 12 in combination with one or more of Elements 13-16; Element 15 with Element 16.

In another embodiment, the present invention provides a method of promoting angiogenesis in a subject, the method comprising administering to the subject in need thereof a composition comprising decellularized preterm placental tissue, wherein the preterm placental tissue is obtained from an animal in gestation having at least about 1 week to about 20 weeks remaining in a normal gestation period of the animal. This embodiment may be combined in combination with one or more of the following elements: Element 17: the method, wherein the decellularized preterm placental tissue comprises one or more of an amnion layer, a chorion layer, and an allantois layer; Element 18: the method, wherein the decellularized preterm placental tissue is acellular; Element 19: the method, further comprising one or more cells; Element 20: Element 19, wherein the cells are selected from the group consisting of embryonic stem cells, mesenchymal stem cells, progenitor cells, hematopoietic stem cells, other tissue specific stem cells, induced pluripotent stem cells, endothelial cells, smooth muscle cells, cardiomyocyte, fibroblasts, beta cells, white blood cells, macrophage, neurons, Schwann cells, chondrocytes, satellite cells, and combinations thereof; Element 21: Element 19 or Element 20, wherein the cells are human cells; Element 22: the method, wherein the decellularized preterm placental tissue comprises one or more growth factors in an amount at least about at least about 120% of the amount of growth factors present in decellularized placental tissue obtained from a full-term placenta of the same animal; Element 23: the method, wherein the decellularized preterm placental tissue comprises one or more extracellular matrix components in an amount that is at least about 120% of the amount of extracellular matrix components present in decellularized placental tissue obtained from a full-term placenta of the same animal; Element 24: the method, wherein the animal is a mammal; Element 25: Element 24, wherein the mammal is selected from the group consisting of bovine, porcine, murine, ovine, equine, canine, caprine, rabbit, primate, and feline; and Element 26: the method, wherein the composition further comprises one or more an active agent selected from the group consisting of an antibiotic, antifungal agent, anti-viral agent, anti-pain agent, anesthetic, analgesic, steroidal anti-inflammatory, non-steroidal anti-inflammatory, anti-neoplastic, anti-spasmodic, hormone, enzyme, enzyme inhibitor, anticoagulant, antithrombic agent, polypeptide, oligonucleotide, polynucleotide, nucleoprotein, compound modulating cell migration, compound modulating proliferation and growth of tissue, and vasodilating agent. This embodiment may be combined in combination with one or more of any element listed above. Specific combinations include Element 17 in combination with one or more of Elements 18-26; Element 18 in combination with one or more of Elements 19-26; Element 19 in combination with one or more of Elements 20-26; Element 22 in combination with one or more of Elements 23-26; Element 23 in combination with one or more of Elements 24-26; and Element 24 in combination with one or both of Elements 25 and 26.

In another embodiment, the present invention provides a method of treating a wound in a subject, the method comprising administering to the subject in need thereof a composition comprising decellularized preterm placental tissue, wherein the preterm placental tissue is obtained from an animal in gestation having at least about 1 week to about 20 weeks remaining in a normal gestation period of the animal. This embodiment may be combined in combination with one or more of any element listed above. Specific combinations include Element 17 in combination with one or more of Elements 18-26; Element 18 in combination with one or more of Elements 19-26; Element 19 in combination with one or more of Elements 20-26; Element 22 in combination with one or more of Elements 23-26; Element 23 in combination with one or more of Elements 24-26; and Element 24 in combination with one or both of Elements 25 and 26.

In another embodiment, the present invention provides a method of stimulating tissue regeneration in a subject, the method comprising administering to the subject in need thereof a composition comprising decellularized preterm placental tissue, wherein the preterm placental tissue is obtained from an animal in gestation having at least about 1 week to about 20 weeks remaining in a normal gestation period of the animal. This embodiment may be combined in combination with one or more of any element listed above. Specific combinations include Element 17 in combination with one or more of Elements 18-26; Element 18 in combination with one or more of Elements 19-26; Element 19 in combination with one or more of Elements 20-26; Element 22 in combination with one or more of Elements 23-26; Element 23 in combination with one or more of Elements 24-26; and Element 24 in combination with one or both of Elements 25 and 26.

EXAMPLES

Example 1. Preterm placental tissues were obtained from pigs in gestation at 60, 63, 74, 79, 88, and 95 days of gestation. The preterm placental tissues were tested for mechanical strength and for levels of growth factor bFGF and hyaluronic acid. A universal test machine (Testresources Inc, MN) was used for the mechanical test. Preterm placental tissue samples (sample width 20 mm, gauge length 20 mm) were pulled at rate of 0.1 inch per minute. The maximum force the sample withstood before breaking was recorded.

Figure 2:
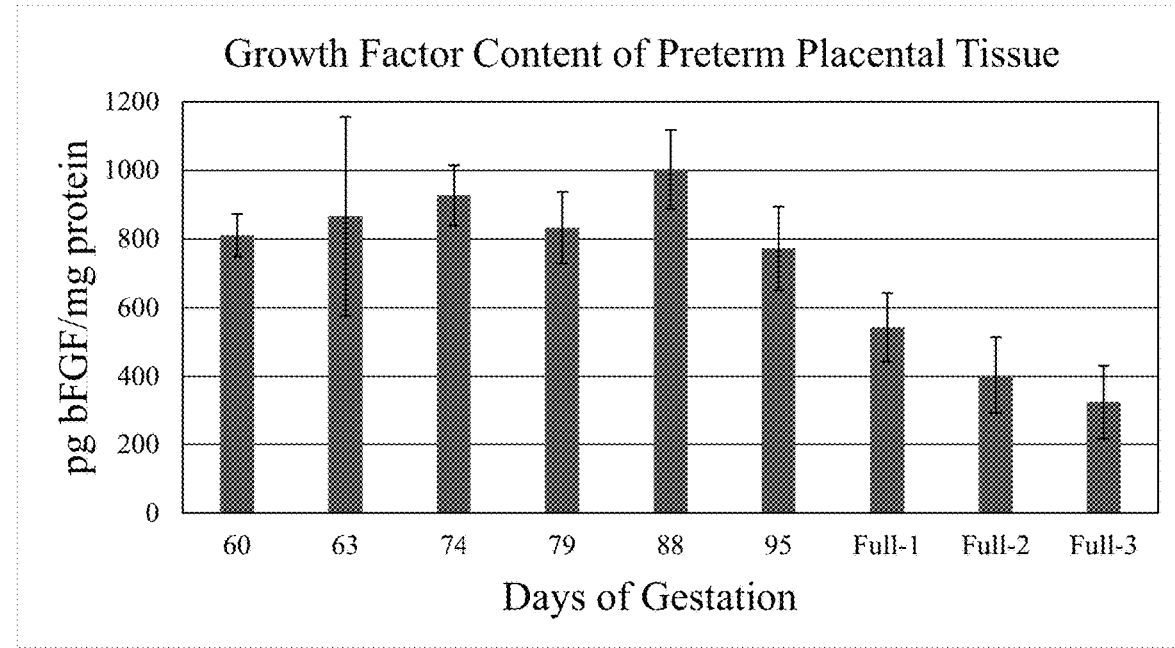
FIG. 2 depicts the levels of bFGF in preterm placental membranes obtained from pigs of different gestational periods.
Figure 3:
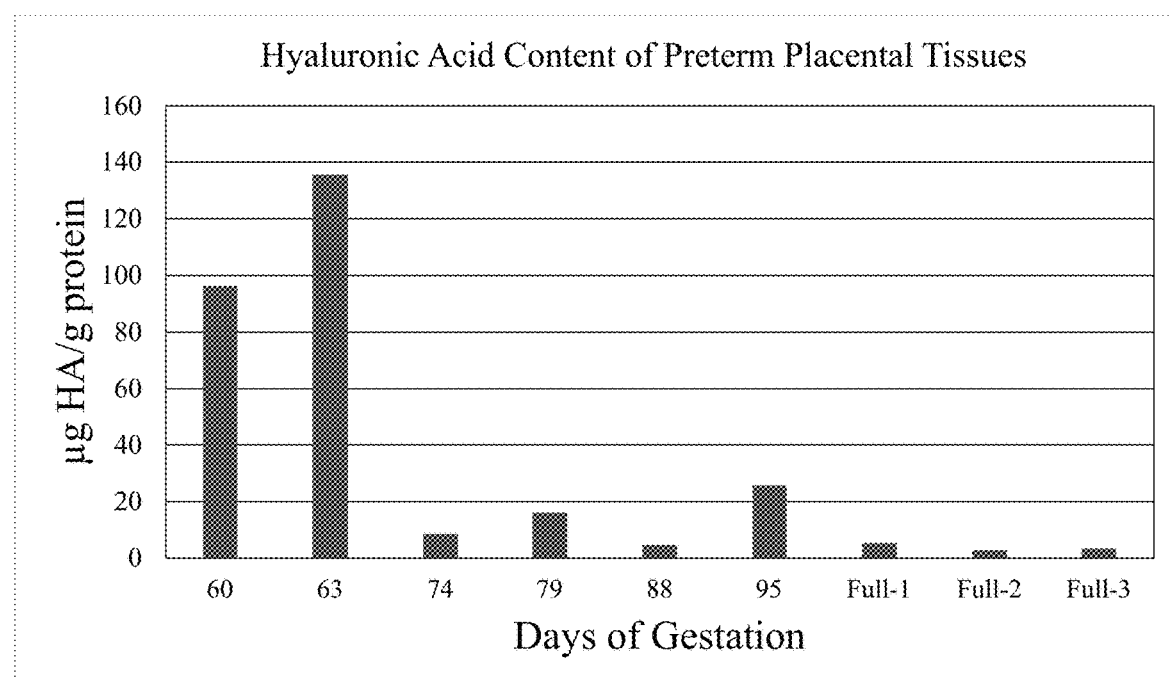
FIG. 3 depicts the levels of hyaluronic acid in preterm placental membranes obtained from pigs of different gestational periods.

As shown in FIG. 1, preterm placental tissue obtained at gestation day 88 and 95 exhibited greater mechanical strength when compared to full term placental tissue. Further, preterm placental tissues obtained between gestation day 60 and day 95 had higher bFGF levels and hyaluronic acid (HA) content when compared to full-term placental tissue (see FIG. 2 and FIG. 3).

Figure 4:
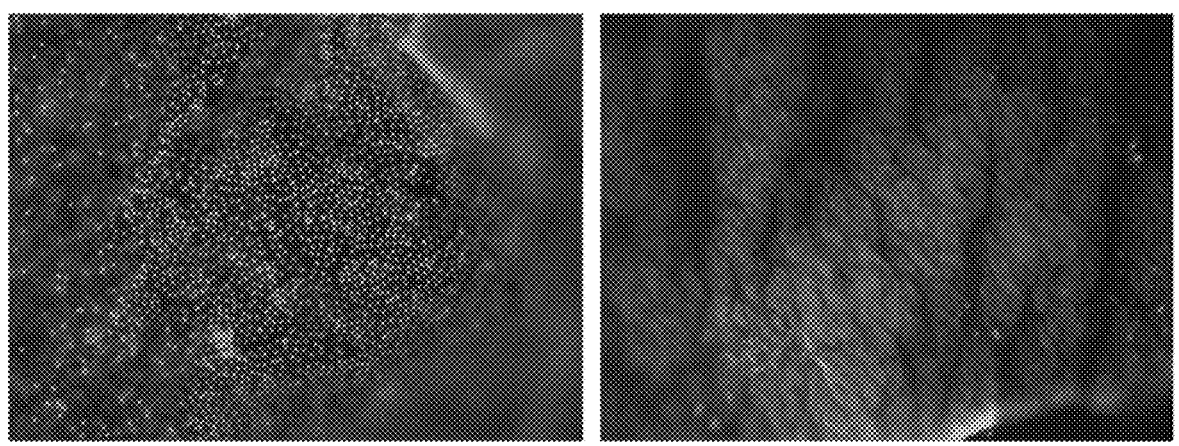
FIG. 4 shows a native porcine amnion layer (A) and an amnion layer decellularized with 0.5% SDS (B).

Example 2. Preterm placental tissues were obtained from pigs and the amnion layer was separated from the placental tissues and decellularized by treating with 0.5% SDS for 5 days. The amnion layer was stained with DAPI and observed under a microscope for evidence of any intact cells. As shown in FIG. 4, treatment with 0.5% SDS was sufficient to decellularize the amnion layer.

Figure 5:
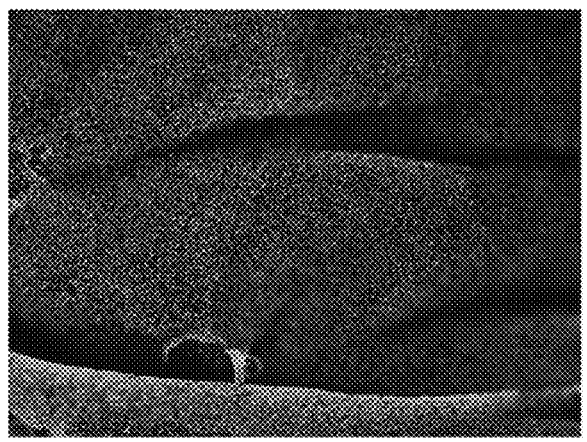
FIG. 5 shows a native bovine allantois layer (A) and an allantois layer decellularized with 0.5% SDS (B).
Figure 5:
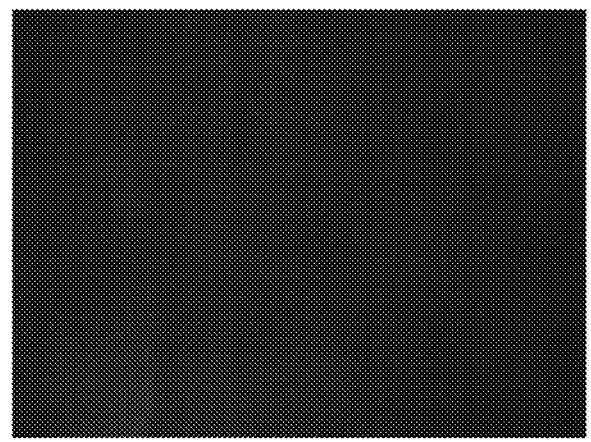
Figure 6:
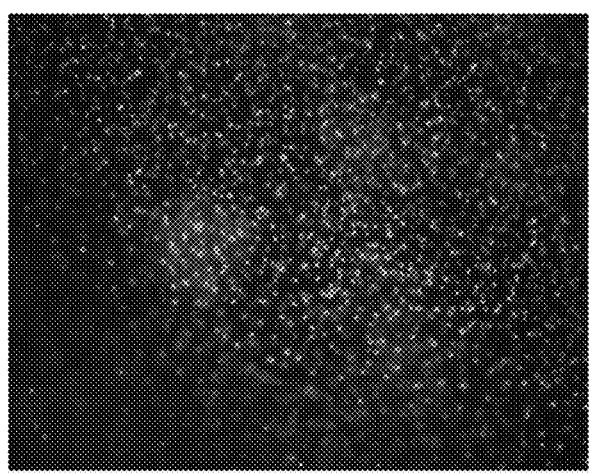
FIG. 6 shows a native bovine chorion layer (A) and a chorion layer decellularized with 0.5% SDS (B).
Figure 6:
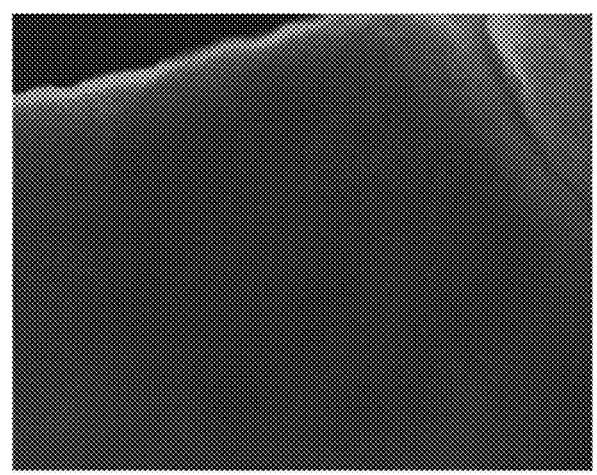

Similar methods were used to decellularize a bovine allantois layer and chorion layer. The bovine allantois layer and chorion layer were incubated with 0.5% SDS for 1 day, later stained with DAPI, and visualized under a microscope. As shown in FIG. 5 and FIG. 6, treatment with 0.1% SDS was sufficient to decellularize bovine allantois and chorion layers.

What is claimed is:

1. A composition comprising decellularized preterm placental tissue, wherein the preterm placental tissue is obtained from an animal in gestation having at least about 1 week to about 20 weeks remaining in a normal gestation period of the animal, wherein at least about 80% of a normal gestation period is complete, and wherein the animal is a mammal selected from the group consisting of bovine, equine, ovine, or porcine.

2. The composition of claim 1, wherein the decellularized preterm placental tissue comprises one or more of an amnion layer, a chorion layer, and an allantois layer.

3. The composition of claim 1, wherein the decellularized preterm placental tissue is acellular.

4. The composition of claim 1, further comprising one or more cells.

5. The composition of claim 4, wherein the cells are selected from the group consisting of embryonic stem cells, mesenchymal stem cells, progenitor cells, hematopoietic stem cells, other tissue specific stem cells, induced pluripotent stem cells, endothelial cells, smooth muscle cells, cardiomyocyte, fibroblasts, beta cells, white blood cells, macrophage, neurons, Schwann cells, chondrocytes, satellite cells, and combinations thereof.

6. The composition of claim 5, wherein the cells are human cells.

7. The composition of claim 1, wherein the decellularized preterm placental tissue comprises one or more growth factors in an amount at least about at least about 120% of the amount of growth factors present in decellularized placental tissue obtained from a full-term placenta of the same animal.

8. The composition of claim 1, wherein the decellularized preterm placental tissue comprises one or more extracellular matrix components in an amount that is at least about 120% of the amount of extracellular matrix components present in decellularized placental tissue obtained from a full-term placenta of the same animal.

9. The composition of claim 1, wherein the composition further comprises one or more of an active agent selected from the group consisting of an antibiotic, antifungal agent, anti-viral agent, anti-pain agent, anesthetic, analgesic, steroidal anti-inflammatory, non-steroidal anti-inflammatory, anti-neoplastic, anti-spasmodic, hormone, enzyme, enzyme inhibitor, anticoagulant, antithrombic agent, polypeptide, oligonucleotide, polynucleotide, nucleoprotein, compound modulating cell migration, compound modulating proliferation and growth of tissue, and vasodilating agent.

10. A scaffold comprising decellularized preterm placental tissue incorporated into an encasement structure, wherein the preterm placental tissue is obtained from an animal in gestation having at least about 1 week to about 20 weeks remaining in a normal gestation period of the animal, wherein at least about 80% of a normal gestation period is complete, wherein the animal is a mammal selected from the group consisting of bovine, equine, ovine, or porcine, and wherein the scaffold has a three-dimensional shape that is stable under mechanical stress.

11. The scaffold of claim 10, wherein the decellularized preterm placental tissue comprises one or more of an amnion layer, a chorion layer, and an allantois layer.

12. The scaffold of claim 10, wherein the decellularized preterm placental tissue is acellular.

13. The scaffold of claim 10, further comprising one or more cells.

14. The scaffold of claim 13, wherein the cells are selected from the group consisting of embryonic stem cells, mesenchymal stem cells, progenitor cells, hematopoietic stem cells, other tissue specific stem cells, induced pluripotent stem cells, endothelial cells, smooth muscle cells, cardiomyocyte, fibroblasts, beta cells, and combinations thereof.

15. The scaffold of claim 14, wherein the cells are human cells.

\* \* \* \* \*